(12) United States Patent
Hanson

(10) Patent No.: US 12,266,017 B1
(45) Date of Patent: Apr. 1, 2025

(54) ACCIDENT DETECTION AND RECOVERY

(71) Applicant: Allstate Insurance Company, Northbrook, IL (US)

(72) Inventor: Randall M. Hanson, Lake Ozark, MO (US)

(73) Assignee: Allstate Insurance Company, Northbrook, IL (US)

( * ) Notice: Subject to any disclaimer, the term of this patent is extended or adjusted under 35 U.S.C. 154(b) by 448 days.

(21) Appl. No.: 16/782,555

(22) Filed: Feb. 5, 2020

Related U.S. Application Data

(63) Continuation of application No. 15/681,814, filed on Aug. 21, 2017, now Pat. No. 10,592,990, which is a (Continued)

(51) Int. Cl.
*G06Q 40/08* (2012.01)
*G01P 3/00* (2006.01)
(Continued)

(52) U.S. Cl.
CPC .......... *G06Q 40/08* (2013.01); *G01P 3/00* (2013.01); *G01P 15/00* (2013.01); *G16H 10/60* (2018.01); *H04W 4/023* (2013.01)

(58) Field of Classification Search
None
See application file for complete search history.

(56) References Cited

U.S. PATENT DOCUMENTS 6,076,028 A * 6/2000 Donnelly .............. B60R 21/013
701/45
6,141,611 A * 10/2000 Mackey ................ G07C 5/0891
340/904

(Continued)

FOREIGN PATENT DOCUMENTS

EP 1837839 A1 9/2007
FJ 2128841 A1 12/2009
(Continued)

OTHER PUBLICATIONS

Watthanawisuth, N., et al. "Wireless Black Box Using MEMS Accelerometer and GPS Tracking for Accidental Monitoring of Vehicles—IEEE Conference Publication." IEEE, Wireless Black Box Using MEMS Accelerometer and GPS Tracking for Accidental Monitoring of Vehicles—Jul. 31, 2012, (Year: 2012).*

(Continued)

*Primary Examiner* — Abhishek Vyas
*Assistant Examiner* — Shacole C Tibljas
(74) *Attorney, Agent, or Firm* — Akerman LLP

(57) ABSTRACT

One or more devices in an accident detection and recovery computing system may be configured to determine that vehicle accidents have occurred, collect and analyze accident characteristics and other related data, and providing customized accident recovery services. Mobile computing devices, alone or in combination with vehicle-based systems and external devices, may detect accidents or receive accident indication data. After determining that an accident has occurred, mobile computing devices and/or vehicle-based systems may be configured to determine accident characteristics, retrieve vehicle data and vehicle occupant data from one or external servers, determine the damages or potential damages resulting from the accident, and determine one or more accident recovery options or recommendations based on the accident damages. Various user interface screens may be generated and displayed via the user's mobile device and/or a vehicle-based display device to provide the user with accident information, damages, and recovery options or recommendations.

20 Claims, 7 Drawing Sheets

Related U.S. Application Data continuation of application No. 14/487,899, filed on Sep. 16, 2014, now Pat. No. 9,773,281.

(51) Int. Cl.
*G01P 15/00* (2006.01)
*G16H 10/60* (2018.01)
*H04W 4/02* (2018.01)

(56) References Cited

U.S. PATENT DOCUMENTS

| | | | |
|---|---|---|---|
| 7,133,611 B2 | 11/2006 | Kaneko | |
| 7,133,661 B2 * | 11/2006 | Hatae | G08B 13/19647 |
| | | | 455/418 |
| 8,019,629 B1 * | 9/2011 | Medina, III | G06Q 40/08 |
| | | | 705/4 |
| 8,244,291 B2 | 8/2012 | Jorgensen | |
| 8,417,212 B2 * | 4/2013 | Cepuran | H04W 76/50 |
| | | | 455/445 |
| 8,799,034 B1 * | 8/2014 | Brandmaier | G07C 5/008 |
| | | | 705/4 |
| 8,825,277 B2 * | 9/2014 | McClellan | G06Q 10/06 |
| | | | 701/34.2 |
| 2003/0200123 A1 | 10/2003 | Burge et al. | |
| 2003/0233261 A1 | 12/2003 | Kawahara et al. | |
| 2004/0088090 A1 | 5/2004 | Wee | |
| 2005/0021374 A1 * | 1/2005 | Allahyari | G06Q 40/08 |
| | | | 705/400 |
| 2006/0212195 A1 | 9/2006 | Veith et al. | |
| 2008/0252487 A1 * | 10/2008 | McClellan | G06Q 10/06398 |
| | | | 340/936 |
| 2008/0306996 A1 * | 12/2008 | McClellan | G06Q 10/06 |
| 2010/0123565 A1 | 5/2010 | Kaufman et al. | |
| 2010/0286993 A1 * | 11/2010 | Lovelace | G16H 10/60 |
| | | | 705/14.58 |
| 2011/0153367 A1 | 6/2011 | Amigo et al. | |
| 2012/0059676 A1 | 3/2012 | King | |
| 2013/0169410 A1 | 7/2013 | Amselem | |
| 2013/0226369 A1 | 8/2013 | Yorio et al. | |
| 2013/0267194 A1 * | 10/2013 | Breed | G06V 10/143 |
| | | | 455/404.2 |
| 2014/0207341 A1 * | 7/2014 | Wanami | B60R 21/0136 |
| | | | 701/46 |
| 2014/0249850 A1 | 9/2014 | Woodson et al. | |
| 2014/0288727 A1 * | 9/2014 | Everhart | G07C 5/00 |
| | | | 701/1 |

FOREIGN PATENT DOCUMENTS

| | | |
|---|---|---|
| GB | 2268608 A | 1/1994 |
| WO | 1999031575 A1 | 6/1999 |
| WO | 2012077965 A2 | 6/2012 |
| WO | 2013045839 A1 | 4/2013 |
| WO | 2013150557 A1 | 10/2013 |
| WO | WO-2014207558 A2 * | 12/2014 ......... G01C 21/3461 |

OTHER PUBLICATIONS

Marc E. Berryman; "Automatic Crash Notification and 9-1-1: A Success Story"; dated Aug. 2004.
Arunashish Majumdar et al.; "Telematics in US Auto Insurance"; TATA Consultancy Sevices; © 2011.
Gérard Ségarra; "Telematics At The Rescue Of Road Safety"; date unknown but believed to be prior to the filing of this application.
Tobias Ippisch; "Telematics Data In Motor Insurance: Creating Value By Understanding The Impact Of Accidents On Vehicle Use"; Dissertation No. 3829; dated Oct. 26, 2010.
"The New Auto Insurance Ecosystem: Telematics, Mobility and the Connected Car"; Cognizant Reports; Aug. 2012.
Chris Thompson et al.; "Using Smartphones to Detect Car Accidents and Provide Situational Awareness to Emergency Responders" date unknown but believed to be prior to the filing of this application.
"Telematics Insurance: A Disruptive Innovation"; IBM global Business Services; Sep. 2012.
Milan B. Vukajlovic et al.; "The Practical Design of In-vehicle Telematics Device with GPS and MEMS Accelerometers"; Telfor Journal, vol. 4, No. 2, 2012.
"It's Easy to Get the 5% Discount." USAA. N.p., n.d. Web. Aug. 18, 2016. <https://www.usaa.com/inet/pages/auto_insurance_driving_research_discount_mail?akredire&akredirect=true>.

* cited by examiner

ACCIDENT DETECTION AND RECOVERY

CROSS REFERENCE TO RELATED APPLICATIONS

This application is a continuation of and claims priority to co-pending U.S. application Ser. No. 15/681,814, filed Aug. 21, 2017, and entitled "Accident Detection and Recovery" which is a continuation of and claims priority to U.S. application Ser. No. 14/487,899 (now U.S. Pat. No. 9,773, 281), filed Sep. 16, 2014, and entitled "Accident Detection and Recovery," all of which are incorporated herein by reference in its entirety.

TECHNICAL FIELD

Various aspects of the disclosure generally relate to systems and methods of collecting and analyzing driving data and accident data relating to vehicles and individuals. Specifically, various aspects relate to systems and methods of detecting or determining accidents involving vehicles and individuals, collecting and analyzing accident characteristics and other related data, and providing customized accident recovery services using vehicle-based systems and/or mobile computing devices of vehicle occupants.

BACKGROUND

The collection and analysis of driving data, such as the identification of driving behaviors and traffic accidents, has many applications. For example, insurance companies and financial institutions may offer rate discounts or other financial incentives to customers based on safe driving behaviors and accident-free driving records. Law enforcement or government personnel may collect and analyze driving data and traffic accident statistics to identify dangerous driving roads or times, and to detect moving violations and other unsafe driving behaviors. In other cases, driving data may be used for navigation applications, vehicle tracking and monitoring applications, and on-board vehicle maintenance applications, among others.

Vehicle-based computer systems, such as on-board diagnostics (OBD) systems and telematics devices, may be used in automobiles and other vehicles, and may be capable of collecting various driving data and vehicle sensor data. For example, OBD systems may receive information from the vehicle's on-board computers and sensors in order to monitor a wide variety of information relating to the vehicle systems, such as engine RPM, emissions control, vehicle speed, throttle position, acceleration and braking rates, use of driver controls, etc. Vehicles may also include Global Positioning System (GPS) receivers and devices installed within or operating at the vehicle configured to collect vehicle location and time data. Such vehicle-based systems may be capable of collecting driving data which may be used to perform various driving data analyses such as statistical driving evaluations, driver score calculations, etc. Vehicle-based systems also may be configured to detect the occurrence of traffic accidents, for instance, using vehicle body impact sensors and airbag deployment sensors. However, not all vehicles are equipped with systems capable of collecting, analyzing, and communicating driving data. Moreover, a single vehicle may be used by multiple different drivers, and conversely, a single driver may drive multiple different vehicles. Thus, vehicle driving data and/or accident records collected by vehicle-based systems might not include the vehicle occupants that correspond to the collected driving and accident data.

In contrast to vehicle-based systems, mobile devices such as smartphones, personal digital assistants, tablet computers, and the like, are often carried and/or operated by a single user. Some mobile devices may include movement sensors, such as an accelerometer, gyroscope, speedometer, and/or GPS receivers, capable of detecting movement.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the disclosure relate to systems, apparatuses, computer-implemented methods, and computer-readable media for determining that vehicle accidents have occurred, collecting and analyzing accident characteristics and other related data, and providing customized accident recovery services. In some cases, a mobile computing device within a moving vehicle may be configured to detect that an accident involving the vehicle has occurred. The mobile computing device may detect an accident using movement and location sensors on the device, or may establish communication with one or more vehicle-based devices (e.g., a vehicle control computer, on-board diagnostic system, telematics device, etc.) to receive accident indication data from the vehicle. After determining that an accident has occurred, the mobile device and/or vehicle-based systems may be configured to determine accident characteristics, retrieve vehicle data and vehicle occupant data from one or external servers, determine the damages or potential damages resulting from the accident, and determine one or more accident recovery options or recommendations based on the accident damages. Various user interface screens may be generated and displayed via the user's mobile device and/or a vehicle-based display device to provide the user with accident information, damages, and recovery options or recommendations. The determined damages may include actual and/or potential medical injuries to the vehicle occupants, as well as actual and/or potential property damage from the accident. Accident recovery options and recommendations may include, for example, required or suggested vehicle repairs, vehicle repair locations and estimates, required or suggested medical care for the vehicle occupants, insurance determinations, automatic initiation of insurance claims and title transfer processes, transportation and legal services, and the like.

Other features and advantages of the disclosure will be apparent from the additional description provided herein.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein.

DETAILED DESCRIPTION

In the following description of the various embodiments, reference is made to the accompanying drawings, which form a part hereof, and in which is shown by way of illustration, various embodiments of the disclosure that may be practiced. It is to be understood that other embodiments may be utilized.

As will be appreciated by one of skill in the art upon reading the following disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

Figure 1:
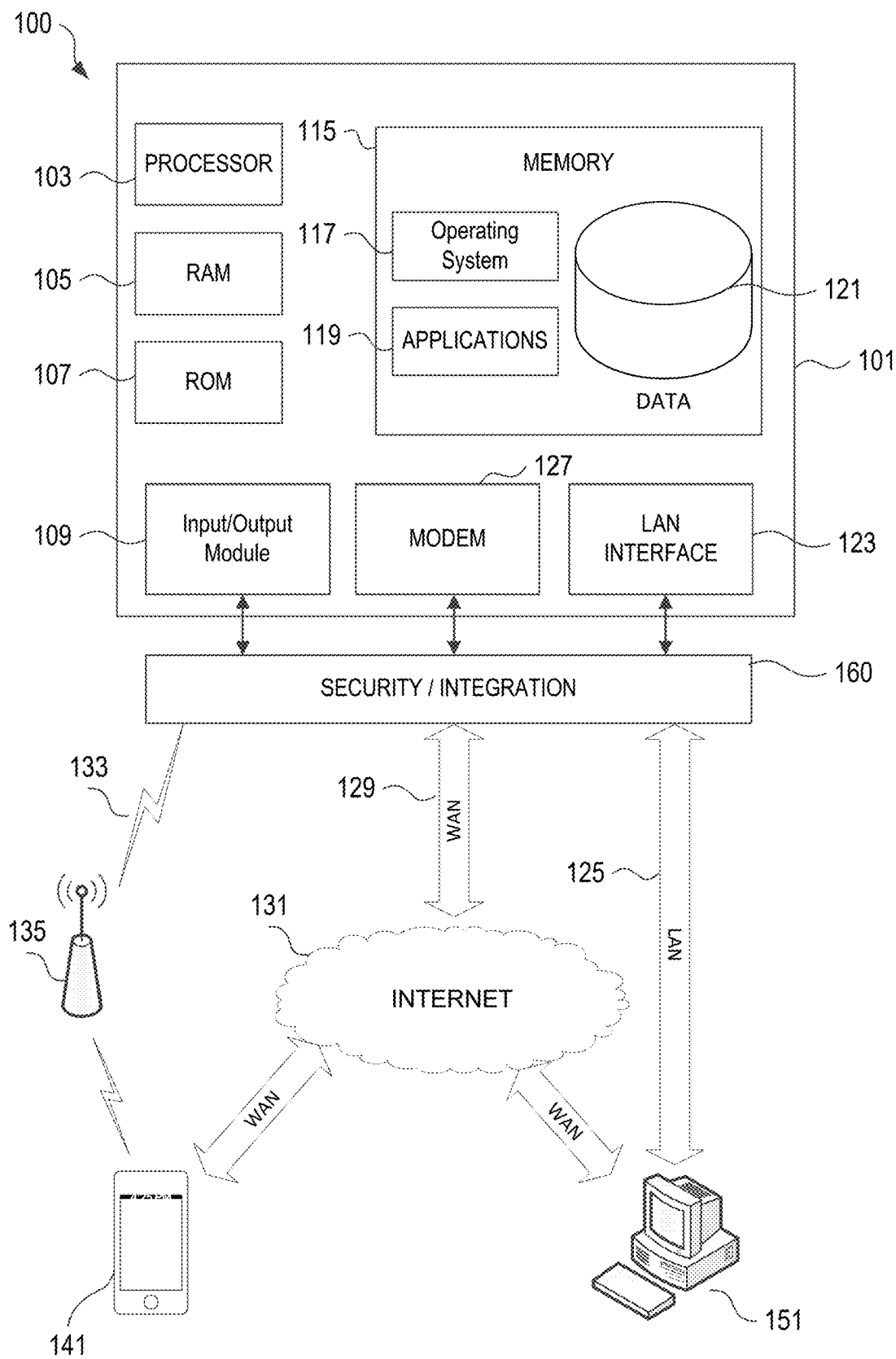
FIG. 1 illustrates computing systems and a network environment that may be used to implement aspects of the disclosure.

FIG. 1 illustrates a block diagram of a computing device (or system) 101 in a computer system 100 that may be used according to one or more illustrative embodiments of the disclosure. The device 101 may have a processor 103 for controlling overall operation of the device 101 and its associated components, including RAM 105, ROM 107, input/output module 109, and memory 115. The computing device 101, along with one or more additional devices (e.g., terminals 141 and 151, security and integration hardware 160) may correspond to any of multiple systems or devices, such as a personal mobile computing device, a vehicle-based computing system, or a computer server, configured as described herein for determining vehicle accidents, collecting and analyzing accident characteristics and other related data, and providing customized accident recovery services.

Input/Output (I/O) 109 may include a microphone, keypad, touch screen, and/or stylus through which a user of the computing device 101 may provide input, and may also include one or more of a speaker for providing audio output and a video display device for providing textual, audiovisual and/or graphical output. Software may be stored within memory 115 and/or storage to provide instructions to processor 103 for enabling device 101 to perform various actions. For example, memory 115 may store software used by the device 101, such as an operating system 117, application programs 119, and an associated internal database 121. The various hardware memory units in memory 115 may include volatile and nonvolatile, removable and non-removable media implemented in any method or technology for storage of information such as computer readable instructions, data structures, program modules or other data. Certain devices/systems within an accident detection and recovery system may have minimum hardware requirements in order to support sufficient storage capacity, analysis capacity, network communication, etc. For instance, in some embodiments, one or more nonvolatile hardware memory units having a minimum size (e.g., at least 1 gigabyte (GB), 2 GB, 5 GB, etc.), and/or one or more volatile hardware memory units having a minimum size (e.g., 256 megabytes (MB), 512 MB, 1 GB, etc.) may be used in a device 101 (e.g., a mobile computing device 101, vehicle-based computing system 101, external server 101, etc.), in order to store and execute an accident detection and recovery software application, collect and analyze accident data, determine accident characteristics, retrieve data associated with the vehicle and/or vehicle occupants, determine and provide various accident recovery services to users, etc. Memory 115 also may include one or more physical persistent memory devices and/or one or more non-persistent memory devices. Memory 115 may include, but is not limited to, random access memory (RAM) 105, read only memory (ROM) 107, electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 103.

Processor 103 may include a single central processing unit (CPU), which may be a single-core or multi-core processor (e.g., dual-core, quad-core, etc.), or may include multiple CPUs. Processor(s) 103 may have various bit sizes (e.g., 16-bit, 32-bit, 64-bit, 96-bit, 128-bit, etc.) and various processor speeds (ranging from 100 MHz to 5 Ghz or faster). Processor(s) 103 and its associated components may allow the system 101 to execute a series of computer-readable instructions, for example, to execute an accident detection and recovery software application that receives and stores accident data from vehicle-based systems, mobile computing devices, and/or external servers, analyzes the accident data, and determines characteristics and related data to provide custom accident recovery services.

The computing device (e.g., a mobile computing device, a vehicle-based device, external server, etc.) may operate in a networked environment 100 supporting connections to one or more remote computers, such as terminals 141 and 151. The terminals 141 and 151 may be personal computers, servers (e.g., web servers, database servers), or mobile communication devices (e.g., mobile phones, portable computing devices, on-board vehicle-based computing systems, and the like), and may include some or all of the elements described above with respect to the computing device 101. The network connections depicted in FIG. 1 include a local area network (LAN) 125 and a wide area network (WAN) 129, and a wireless telecommunications network 133, but may also include other networks. When used in a LAN networking environment, the computing device 101 may be connected to the LAN 125 through a network interface or adapter 123. When used in a WAN networking environment, the device 101 may include a modem 127 or other means for establishing communications over the WAN 129, such as network 131 (e.g., the Internet). When used in a wireless telecommunications network 133, the device 101 may include one or more transceivers, digital signal processors, and additional circuitry and software for communicating with wireless computing devices 141 (e.g., mobile phones, portable computing devices, on-board vehicle-based computing systems, etc.) via one or more network devices 135 (e.g., base transceiver stations) in the wireless network 133.

Also illustrated in FIG. 1 is a security and integration layer 160, through which communications may be sent and managed between the device 101 (e.g., a user's personal mobile device, a vehicle-based system, an accident detection and recovery server or other external server, etc.) and the remote devices (141 and 151) and remote networks (125, 129, and 133). The security and integration layer 160 may comprise one or more separate computing devices, such as web servers, authentication servers, and/or various networking components (e.g., firewalls, routers, gateways, load balancers, etc.), having some or all of the elements described above with respect to the computing device 101. As an example, a security and integration layer 160 of a mobile computing device, vehicle-based device, or a server operated by an insurance provider, financial institution, governmental entity, or other organization, may comprise a set of web application servers configured to use secure protocols and to insulate the server 101 from external devices 141 and 151. In some cases, the security and integration layer 160 may correspond to a set of dedicated hardware and/or software operating at the same physical location and under the control of same entities as driving data analysis server 101. For example, layer 160 may correspond to one or more dedicated web servers and network hardware in an organizational datacenter or in a cloud infrastructure supporting a cloud-based driving data analysis system. In other examples, the security and integration layer 160 may correspond to separate hardware and software components which may be operated at a separate physical location and/or by a separate entity.

As discussed below, the data transferred to and from various devices in the computing system 100 may include secure and sensitive data, such as driving data, driving locations, vehicle data, and confidential individual data such as insurance data and medical data associated with vehicle occupants. Therefore, it may be desirable to protect transmissions of such data by using secure network protocols and encryption, and also to protect the integrity of the data when stored on in a database or other storage in a mobile device, driving data analysis server, or other computing devices in the system 100, by using the security and integration layer 160 to authenticate users and restrict access to unknown or unauthorized users. In various implementations, security and integration layer 160 may provide, for example, a file-based integration scheme or a service-based integration scheme for transmitting data between the various devices in a system 100. Data may be transmitted through the security and integration layer 160, using various network communication protocols. Secure data transmission protocols and/or encryption may be used in file transfers to protect to integrity of the driving data, for example, File Transfer Protocol (FTP), Secure File Transfer Protocol (SFTP), and/or Pretty Good Privacy (PGP) encryption. In other examples, one or more web services may be implemented within the various devices 101 in the system 100 and/or the security and integration layer 160. The web services may be accessed by authorized external devices and users to support input, extraction, and manipulation of the data (e.g., driving data, location data, confidential personal data, etc.) between the various devices 101 in the system 100. Web services built to support system 100 may be cross-domain and/or cross-platform, and may be built for enterprise use. Such web services may be developed in accordance with various web service standards, such as the Web Service Interoperability (WS-I) guidelines. In some examples, a movement data and/or driving data web service may be implemented in the security and integration layer 160 using the Secure Sockets Layer (SSL) or Transport Layer Security (TLS) protocol to provide secure connections between servers 101 and various clients 141 and 151 (e.g., mobile devices, data analysis servers, etc.). SSL or TLS may use HTTP or HTTPS to provide authentication and confidentiality. In other examples, such web services may be implemented using the WS-Security standard, which provides for secure SOAP messages using XML encryption. In still other examples, the security and integration layer 160 may include specialized hardware for providing secure web services. For example, secure network appliances in the security and integration layer 160 may include built-in features such as hardware-accelerated SSL and HTTPS, WS-Security, and firewalls. Such specialized hardware may be installed and configured in the security and integration layer 160 in front of the web servers, so that any external devices may communicate directly with the specialized hardware.

Although not shown in FIG. 1, various elements within memory 115 or other components in system 100, may include one or more caches, for example, CPU caches used by the processing unit 103, page caches used by the operating system 117, disk caches of a hard drive, and/or database caches used to cache content from database 121. For embodiments including a CPU cache, the CPU cache may be used by one or more processors in the processing unit 103 to reduce memory latency and access time. In such examples, a processor 103 may retrieve data from or write data to the CPU cache rather than reading/writing to memory 115, which may improve the speed of these operations. In some examples, a database cache may be created in which certain data from a database 121 (e.g., a driving or accident database, a vehicle database, insurance customer database, etc.) is cached in a separate smaller database on an application server separate from the database server. For instance, in a multi-tiered application, a database cache on an application server can reduce data retrieval and data manipulation time by not needing to communicate over a network with a back-end database server. These types of caches and others may be included in various embodiments, and may provide potential advantages in certain implementations of retrieving driving, vehicle data, and individual data, such as faster response times and less dependence on network conditions when transmitting/receiving accident detection and recovery software applications (or application updates), driving data, vehicle and occupant data, etc.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, and WiMAX, is presumed, and the various computer devices and system components described herein may be configured to communicate using any of these network protocols or technologies.

Additionally, one or more application programs 119 may be used by the various computing devices 101 within an accident detection and recovery system 100 (e.g., accident detection software applications, customized accident recovery software applications, etc.), including computer executable instructions for receiving and storing driving data from vehicle-based systems and/or mobile computing devices, analyzing the driving data to determine accidents and accident characteristics, retrieve various vehicle data and individual data relating the vehicle occupants, determining and providing custom accident recovery services based on the retrieved data, and performing other related functions as described herein.

Figure 2:
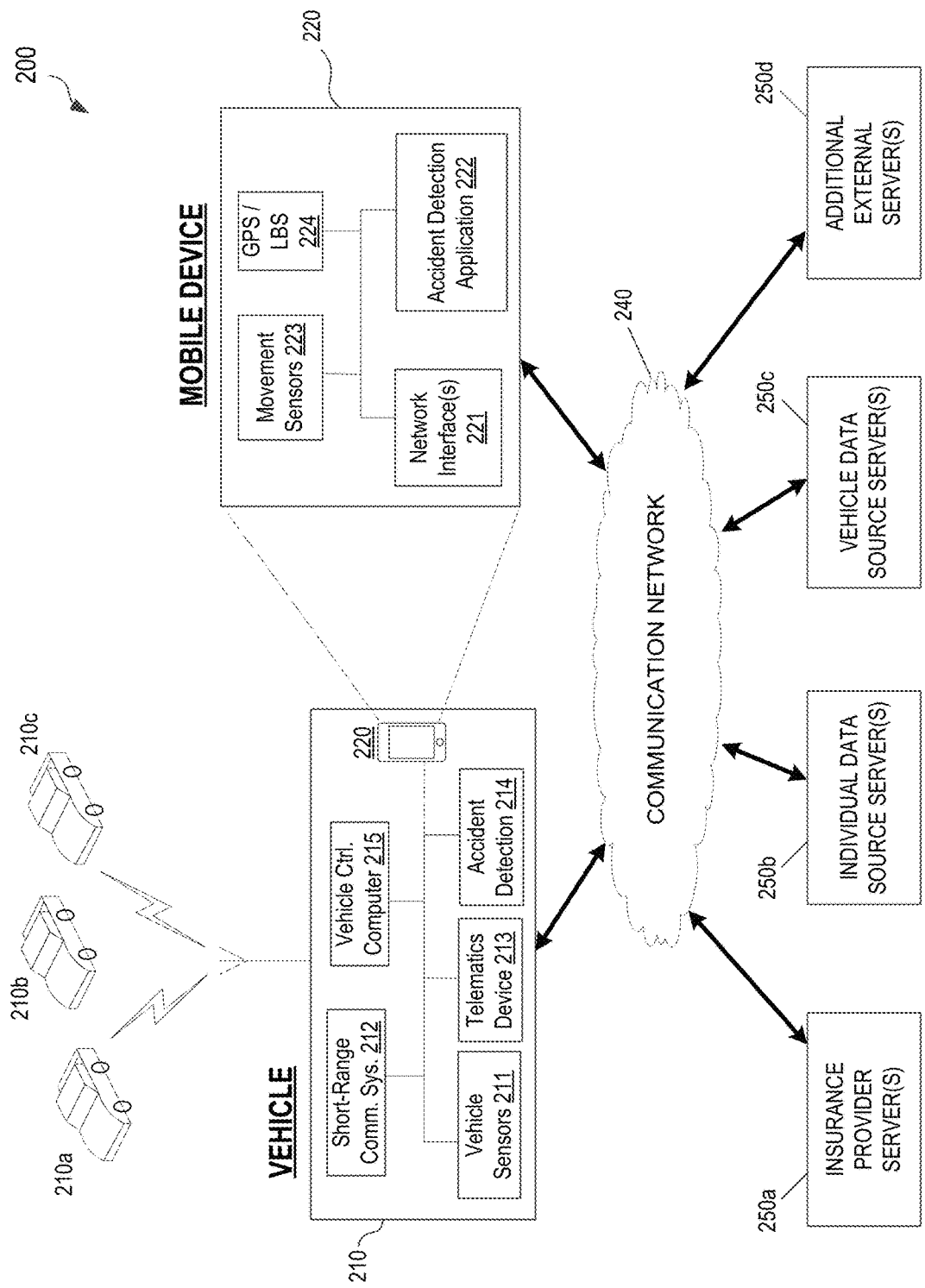
FIG. 2 is an example vehicle accident detection and recovery system, including vehicle-based systems, a personal mobile device, and various external servers accessible via a communication network, according to one or more aspects of the disclosure.

FIG. 2 is a diagram showing an example accident detection and recovery system 200. In this example, the system 200 includes a vehicle 210 containing a number of vehicle-based systems 211-215, and a personal mobile device 220 containing a number of software and/or hardware components. The vehicle 210 and the personal mobile device 220 may communicate with each other wireless networks or wired connections (e.g., for devices physically docked in vehicles), and each may communicate with one or more additional vehicles 210a-210c, additional mobile computing devices, and/or a number of external computer servers 250a-250d over one or more communication networks 240.

As discussed below, the components of accident detection and recovery system 200, operating individually or using communication and collaborative interaction, may perform such features and functions such as determining vehicle accidents and accident characteristics, retrieving data associated with the vehicle and/or vehicle occupants, determining and providing customized accident recovery services to users, and the like. To perform such features and functions, the components shown in FIG. 2 each may be implemented in hardware, software, or a combination of the two. Additionally, each component of the accident detection and recovery system 200 may include a computing device (or system) having some or all of the structural components described above for computing device 101, such as processors, memory units storing operating systems and applications, network interfaces, I/O components, and the like. As shown in FIG. 2, certain accident detection and recovery systems 200 may include a mobile device 220 located within a vehicle 210, such as a driver's or passengers smartphone, tablet computer, or other personal mobile device. In other examples, accident detection and recovery systems 200 may include communication and collaboration among one or more vehicles 210 and/or multiple mobile devices 220 which may be within a single vehicle 210 or within multiple different vehicles 210. As discussed below, some examples of accident detection and recovery systems 200 may include the vehicle-based systems (e.g., 214) of a single vehicle 210, and such systems may perform the features and functionality without needing to communicate or collaborate with any mobile devices 220 and/or other external devices and systems. Other examples of accident detection and recovery systems 200 may include only a mobile device 220 executing one or more software applications (e.g., 222), and such systems may perform the features and functionality without needing to communicate with any vehicles or vehicle-based systems, and/or any other external devices and systems.

Vehicles 210, 210a, 210b, and 210c (collectively "vehicles 210") in the accident detection and recovery system 200 may be, for example, automobiles, motorcycles, scooters, buses, recreational vehicles, boats, or any other vehicles that may potentially be involved in accidents. Each vehicle 210 may include vehicle operation sensors 211 capable of detecting and recording various conditions at the vehicle and operational parameters of the vehicle. For example, sensors 211 may detect and store data corresponding to the vehicle's location (e.g., GPS coordinates), time, travel time, speed and direction, rates of acceleration or braking, gas mileage, and specific instances of sudden acceleration, braking, swerving, and distance traveled. Sensors 211 also may detect and store data received from the vehicle's 210 internal systems, such as impact to the body of the vehicle, air bag deployment, headlights usage, brake light operation, door opening and closing, door locking and unlocking, cruise control usage, hazard lights usage, windshield wiper usage, horn usage, turn signal usage, seat belt usage, phone and radio usage within the vehicle, autonomous driving system usage, maintenance performed on the vehicle, and other data collected by the vehicle's computer systems, including the vehicle OBD.

Additional sensors 211 may detect and store the external driving conditions, for example, external temperature, rain, snow, light levels, and sun position for driver visibility. For example, external cameras and proximity sensors 211 may detect other nearby vehicles, vehicle spacing, traffic levels, road conditions, traffic obstructions, animals, cyclists, pedestrians, and other conditions that may relate to vehicle accidents and accident characteristics. Sensors 211 also may detect and store data relating to moving violations and the observance of traffic signals and signs by the vehicles 210. Additional sensors 211 may detect and store data relating to the maintenance of the vehicles 210, such as the engine status, oil level, engine coolant temperature, odometer reading, the level of fuel in the fuel tank, engine revolutions per minute (RPMs), software upgrades, and/or tire pressure.

Vehicles sensors 211 also may include cameras and/or proximity sensors capable of recording conditions inside or outside of the vehicles 210. For example, internal cameras may detect conditions such as the identity of the driver (e.g., using facial recognition software), the number of the occupants, the types of occupants (e.g. adults, children, teenagers, pets, etc.), and the seating/positioning of the occupants in the vehicles. Internal cameras also may detect potential sources of driver distraction within the vehicle, such as pets, phone usage, and unsecured objects in the vehicle. Sensors 211 also may be configured to collect data identifying a current driver from among a number of different possible drivers, for example, based on driver's seat and mirror positioning, driving times and routes, radio usage, etc. Sensors 211 also may be configured to collect data relating to a driver's movements or the condition of a driver. For example, vehicles 210 may include sensors that monitor a driver's movements, such as the driver's eye position and/or head position, etc. Additional sensors 211 may collect data regarding the physical or mental state of the driver, such as fatigue or intoxication. The condition of the driver may be determined through the movements of the driver or through other sensors, for example, sensors that detect the content of alcohol in the air or blood alcohol content of the driver, such as a breathalyzer.

Certain vehicle sensors 211 also may collect information regarding the vehicle's location, current and past driving routes, in order to classify the type of trip (e.g. work or school commute, shopping or recreational trip, unknown new route, etc.). In certain embodiments, sensors and/or cameras 211 may determine when and how often the vehicles 210 stay in a single lane or stray into other lanes. A Global Positioning System (GPS), locational sensors positioned inside the vehicles 210, and/or locational sensors or devices external to the vehicles 210 may be used to determine the route, lane position, road-type (e.g. highway, entrance/exit ramp, residential area, etc.) and other vehicle position/location data which may be used to analyze accidents and accident characteristics.

The data collected by vehicle sensors 211 may be stored and analyzed within the respective vehicles 210, for example, in optional accident detection and analysis devices 214 and/or accident detection and analysis software applications 214, which may be integrated into or installed at the vehicle 210. In other cases, the data collected by vehicle sensors 211 may be transmitted to one or more external devices for analysis, such as a personal mobile device 220 or external server 250. Additionally, as shown in FIG. 2, sensor data from one vehicle 210 may be transmitted via a short-range communication systems 212 to other nearby vehicles 210a-210, and vice versa. The sensor data also may be transmitted from vehicles 210 via a telematics device 213 or other network interface(s) to one or more remote computing devices, such as one or more personal mobile devices 220, insurance system servers 250a, and/or other external servers 250.

Short-range communication systems 212 may be vehicle-based data transmission systems configured to transmit various (e.g., driving data, vehicle data, insurance data, driver and passenger data, etc.) to other nearby vehicles, and to receive corresponding data from other nearby vehicles. In some examples, communication systems 212 may use the dedicated short-range communications (DSRC) protocols and standards to perform wireless communications between vehicles. In the United States, 75 MHz in the 5.850-5.925 GHz band have been allocated for DSRC systems and applications, and various other DSRC allocations have been defined in other countries and jurisdictions. However, short-range communication systems 212 need not use DSRC, and may be implemented using other short-range wireless protocols in other examples, such as WLAN communication protocols (e.g., IEEE 802.11), Bluetooth (e.g., IEEE 802.15.1), or one or more of the Communication Access for Land Mobiles (CALM) wireless communication protocols and air interfaces. The vehicle-to-vehicle (V2V) transmissions between the short-range communication systems 212 may be sent via DSRC, Bluetooth, satellite, GSM infrared, IEEE 802.11, WiMAX, RFID, and/or any suitable wireless communication media, standards, and protocols. In certain systems, short-range communication systems 212 may include specialized hardware installed in vehicles 210 (e.g., transceivers, antennas, etc.), while in other examples the communication systems 212 may be implemented using existing vehicle hardware components (e.g., radio and satellite equipment, navigation computers) or may be implemented by software running on the mobile devices 220 of drivers and passengers within the vehicles 210.

V2V communications also may include vehicle-to-infrastructure (V2I) communications, such as transmissions from vehicles to non-vehicle receiving devices, for example, toll booths, rail road crossings, and road-side traffic monitoring devices. Certain V2V communication systems may periodically broadcast data from a vehicle 210 to any other vehicle, or other infrastructure device capable of receiving the communication, within the range of the vehicle's transmission capabilities. The range of V2V communications and V2I communications may depend on the wireless communication standards and protocols used, the transmission/reception hardware (e.g., transceivers, power sources, antennas), and other factors. Short-range V2V (and V2I) communications may range from just a few feet to many miles, and different types of accident data and characteristics may be determined depending on the range of the V2V communications. For example, V2V communications ranging only a few feet may be sufficient for an accident detection device or application 214 in a vehicle 210 to determine which other vehicle(s) 210 were also involved in the accident, as well as the angle of impact, an initial accident cause or fault determination (e.g., one vehicle was tailgating or cut-off another vehicle), whereas longer communications may allow an accident detection device or application 214 to determine additional types of accident characteristics (e.g., weather conditions, traffic density, road conditions and other safety hazards, etc.).

When accident-related data, accident characteristics, vehicle data, driver or passenger data, or any other data is transmitted by vehicles 210, the transmission may depend on the protocols and standards used for the V2V and V2I communication, the range of communications, and other factors. In certain examples, vehicles 210 may periodically broadcast corresponding sets of similar vehicle data, such as the vehicle's location (which may include an absolute location in GPS coordinates or other coordinate systems, and/or a relative location with respect to another vehicle or a fixed point), speed, and direction of travel. In certain examples, the nodes in a V2V communication system (e.g., vehicles and other reception devices) may use internal clocks with synchronized time signals, and may send transmission times within V2V communications, so that the receiver may calculate its distance from the transmitting node based on the difference between the transmission time and the reception time. The state or usage of the vehicle's 210 controls and instruments may also be transmitted, for example, whether the vehicle is accelerating, braking, turning, and by how much, and/or which of the vehicle's instruments are currently activated by the driver (e.g., head lights, turn signals, hazard lights, cruise control, 4-wheel drive, traction control, etc.). Vehicle warnings such as detection by the vehicle's 210 internal systems that the vehicle is skidding, that an impact has occurred, or that the vehicle's airbags have been deployed, also may be transmitted in V2V communications.

As shown in FIG. 2, vehicles 210 may use telematics devices 213 to transmit data to and receive data from external servers 250, such as insurance system servers 250a, other external servers 250, and mobile devices 220. Telematics devices 213 may be computing devices containing many or all of the hardware/software components as the computing device 101 depicted in FIG. 1. In some cases, telematics devices 213 may receive vehicle sensor data, operation data, and driving data from vehicle sensors 211, and may transmit the data to one or more external computer systems (e.g., insurance system server 250a of an insurance company, financial institution, or other entity) over a wireless transmission network 240. The telematics devices 213 also may store the type of their respective vehicles 210, for example, the make, model, trim (or sub-model), year, and/or engine specifications, as well as other information such as vehicle owner or driver information, insurance information, warranty information, and financing information for the vehicles 210.

In the example shown in FIG. 2, telematics devices 213 may receive data from vehicle sensors 211, and may transmit the data to a mobile device 220 or external server 250. However, in other examples, one or more of the vehicle sensors 211 or other vehicle-based systems may be configured to receive and transmit data directly from or to other servers 250 or mobile devices 220 without using a telematics device. For instance, telematics devices 213 may be configured to receive and transmit data from certain vehicle sensors 211 or systems, while other sensors or systems may be configured to directly receive and/or transmit data to external servers 250 or mobile devices 220 without using the telematics device 213. Thus, telematics devices 213 may be optional in certain embodiments.

Accident detection and recovery systems 200 may also include one or more mobile devices 220. Mobile devices 220 may be, for example, smartphones or other mobile phones, personal digital assistants (PDAs), tablet computers, and the like, and may include some or all of the elements described above with respect to the computing device 101. As discussed below, a mobile device 220 within a vehicle 210 may, individually or by communication and collaboration with the vehicle 210 and/or other vehicles 210 or mobile devices 220, determine that the mobile device 220 is in vehicle 210 that has been involved in an accident. The mobile device 220 may further receive and/or determine accident characteristics, vehicle data, driver and passenger data, and the like, in order to provide customized accident recovery services. As used herein, a mobile device 220 "within" a vehicle 210 refers to a mobile device 220 that is inside of or otherwise secured to a moving vehicle, for instance, mobile devices 220 in the cabins of automobiles, buses, recreational vehicles, mobile devices 220 traveling in open-air vehicles such as motorcycles, scooters, or boats, and mobile devices 220 in the possession of drivers or passengers of vehicles 210. As shown in this example, a mobile device 210 may be configured to establish communication with vehicle-based devices and various internal components of vehicle 210 via wireless networks or wired connections (e.g., for docked devices), whereby such mobile devices 220 may have secure access to internal vehicle sensors 211 and other vehicle-based systems. However, in other examples, mobile device 220 might not connect to vehicle-based computing devices and internal components, but may operate independently by communicating with vehicles 210 via standard communication interfaces (e.g., short-range communication systems 212, telematics devices 213, etc.), indirectly through external networks 240 and servers 250, or might not communicate at all with vehicles 210.

Mobile devices 220 each may include a network interface 221, which may include various network interface hardware (e.g., adapters, modems, wireless transceivers, etc.) and software components to enable mobile devices 220 to communicate with external servers 250, vehicles 210, and various other external computing devices. One or more specialized software applications, such as accident detection application and/or accident recovery applications 222 may be stored in the memory of the mobile device 220. The accident detection and/or accident recovery application(s) 222 may be received via network interface 221 from the insurance server 250a, vehicles 210, or other application providers (e.g., public or private application stores). Certain accident detection and recovery applications 222 might not include user interface screens (e.g., a driving analysis and accident determination application), while other applications 222 may include user interface screens that support user interaction (e.g., an accident recovery application). Such applications 222 and may be configured to run as user-initiated applications or as background applications. The memory of mobile device 220 also may include databases configured to receive and store accident data, vehicle data, driver or passenger data, insurance data, and the like, associated with one or more drivers and/or vehicles. Although this section describes various accident detection and/or accident recovery software application(s) 222 as executing on mobile devices 220, in various other implementations, some or all of the accident detection and recovery functionality described herein may be implemented within the vehicle 210, via specialized hardware and/or software applications within a vehicle-based system, such as a specialized accident detection and/or recovery hardware device 214, or as software within a telematics device 213 or a vehicle control computer 215, etc.

Like the vehicle-based computing devices in vehicles 210, mobile devices 220 also may include various components configured to generate and/or receive accident data, vehicle data and driver data, or other relevant data for accident detection and recovery. For example, using data from movement sensors 223 (e.g., 1-axis, 2-axis, or 3-axis accelerometers, compasses, speedometers, vibration sensors, gyroscopic sensors, etc.) and/or GPS receivers or other location-based services (LBS) 224, an application 222 may determine that the mobile device 220 is in a moving vehicle, that a driving trip has started or stopped, and/or that a vehicle accident has occurred. The movement sensors 223 and/or GPS receiver or LBS component 224 of a mobile device 220 may also be used to determine driving speeds, routes, accident force and angle of impact, and other accident characteristics and accident-related data.

Mobile computing devices 220 within vehicles may be used to directly detect accident data and characteristics and/or to receive accident data and characteristics from vehicle-based systems. For example, mobile computing device 220 may transmit driving data and accident data, driver data, vehicle data, etc., directly to one or more insurance servers 250a, and thus may be used in conjunction with or instead of telematics devices 213. Additionally, mobile computing devices 220 may be configured to perform the V2V and V2I communications described above, by establishing connections and transmitting/receiving vehicle driving data and accident data to and from other nearby vehicles. Thus, mobile computing device 220 may be used in conjunction with, or instead of, short-range communication system 212 in some examples. In addition, mobile computing device 220 may be used in conjunction with the vehicle control computers 215 for purposes of vehicle control and diagnostics. Moreover, the processing components of the mobile computing devices 220 may be used to identify the drivers and passengers and the time of an accident, analyze accident data and determine accident characteristics, store or update insurance coverage information, and perform other related functions. Therefore, in certain embodiments, mobile computing devices 220 may be used in conjunction with, or in place of, the insurance system server 250a or other external servers 250.

The system 200 also may include one or more external servers 250, such as insurance system servers 250a, an individual data source servers 250b, vehicle data source servers 250c, and other servers 250d, each of which may contain some or all of the hardware/software components as the computing device 101 depicted in FIG. 1. External servers 250 may communicate with vehicles 210, vehicle-based systems 211-215, and mobile devices 220 via one or more communication networks 240. In this example, insurance servers 250a may store insurance data for vehicles and/or customers, including insurance premiums, coverage conditions and amounts, policies deductibles and other insurance policy details, as well as driving histories and accident records for customers and vehicles. Vehicle data sources 250b may be, for example, governmental vehicle record servers, vehicle dealership servers, vehicle maintenance record servers, etc. Certain vehicle data sources servers 250b may store individual vehicle data, for example, a particular vehicle's make, model, year, trim, and any optional features and accessories purchased with the vehicle, as well as the vehicle's VIN, current mileage, accident history, maintenance history, warranty coverage, financing details, etc. In contrast, the same or other vehicle data sources servers 250*b* may store vehicle data that is not specific to an individual vehicle, such as vehicle safety records, reliability data, depreciation and trade-in values for different vehicle makes, models, and features. Individual data sources 250*c* may be, for example, governmental or insurance servers, medical record servers, employer servers, social network servers, etc. Individual data sources servers 250*c* may include any server storing relevant data relating to an individual driver or passenger that may be involved in a vehicle accident, for example, the physical attributes of the individual (e.g., age, gender, height, weight, etc.) and medical data for the individual (e.g., current medical conditions, accident histories, etc.). Additional data source servers 250*d* may include, for example, weather data sources, traffic and road condition data sources, vehicle repair data sources providing repair estimates and appointment scheduling, medical provider data sources providing information and appointment scheduling, legal services data sources, data sources providing towing, taxi, or rental car services, etc. As discussed below, the data from external servers 250 may be used to determine the potential vehicle damages and human medical damages resulting from a vehicle accident, and provide customized accident recovery recommendations and services to vehicle owners and occupants.

Figure 3:
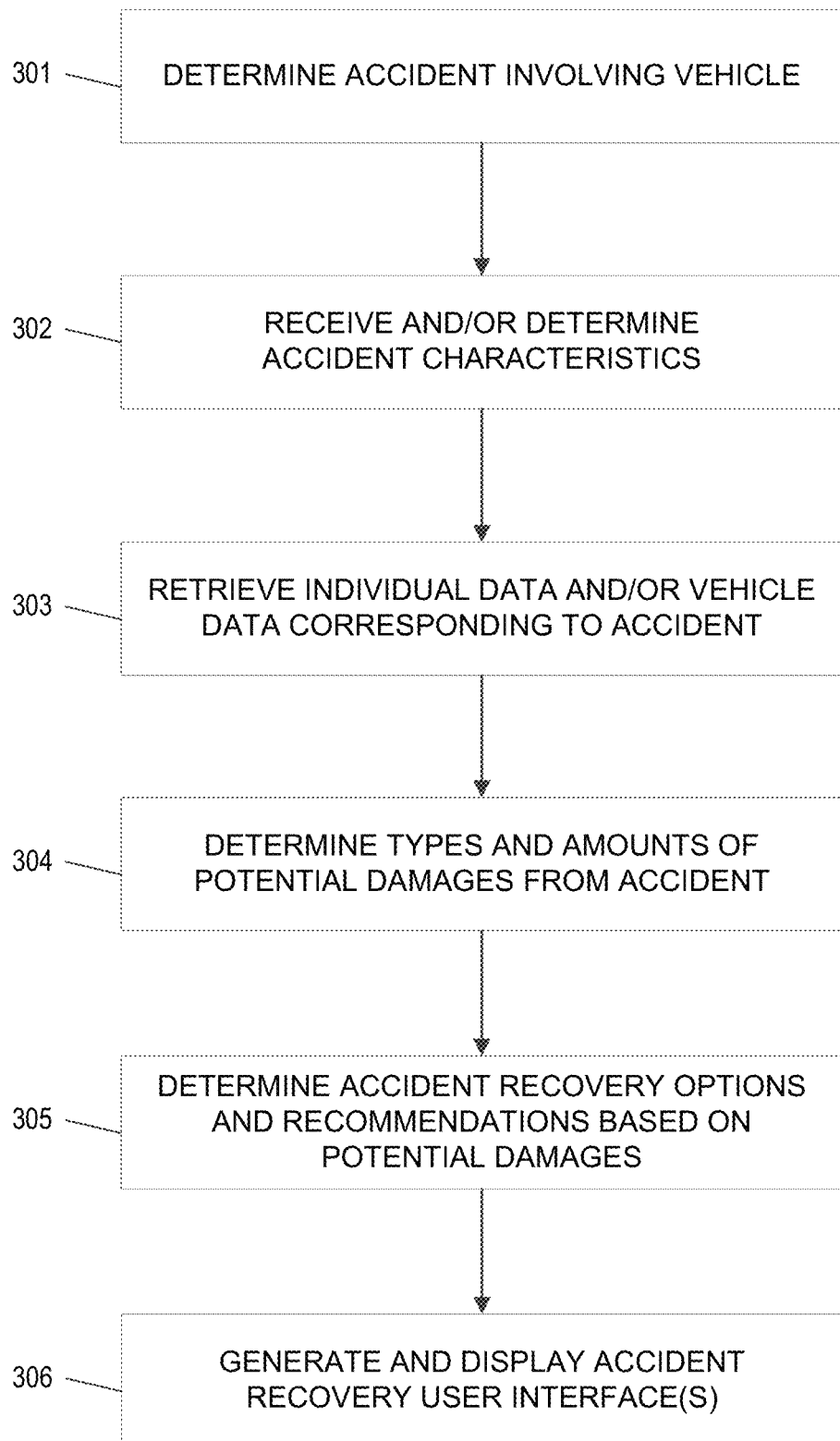
FIG. 3 is a flow diagram illustrating an example method of determining a vehicle accident, and generating and displaying an accident recovery user interface based on various accident characteristics and/or vehicle and individual data, according to one or more aspects of the disclosure.

Referring to FIG. 3, a flow diagram is shown illustrating a process of determining that a vehicle accident has occurred, and generating and displaying an accident recovery user interface based on various accident characteristics, vehicle data, and/or individual data associated with the accident. FIGS. 4A-4H, discussed below in conjunction with FIG. 3, show example user interface display screens of a mobile computing device that illustrate various functionality and features of an accident detection and recovery system. As discussed below, the process steps and functionality described in reference to FIGS. 3 and 4A-4H may be performed by a single mobile computing device 220, such as a smartphone, tablet computer, or PDA of a vehicle driver or passenger. However, in other examples, the process steps and functionality described in reference to FIG. 3, and the user interface display screens shown in FIGS. 4A-4H, may be performed by and displayed on vehicle-based systems, such as vehicle control computers 215, telematics devices 213, on-board navigation systems, or specialized vehicle-based accident detection and recovery devices 214. In still other examples, some features of FIG. 3 may be performed by a mobile computing device 220, while others are performed by a vehicle-based system. Additionally, as discussed below, vehicle-based systems and/or mobile computing devices 220 may communicate and collaborate with the various external servers 250 to communicate accident data, accident characteristics, vehicle data and/or individual data relating a vehicle accident.

In step 301, a determination may be made that one or more vehicles 210 has been involved in an accident. In some cases, the determination in 301 may be performed entirely by a mobile computing device 220 within the vehicle 210, without communicating or collaborating with the vehicle 210, any vehicle-based devices 211-215, or any other device. For example, one or more software applications 222 executing in the mobile device 220 may be configured to monitor the movement sensors 223 and/or GPS receiver or other location-based services (LBS) 224 of the mobile device 220 in order to detect events such as: (i) when the mobile computing device 220 is within (e.g., in or secured to) a moving vehicle; (ii) the beginnings and ends of driving trips; and (iii) vehicle accidents during driving trips. For instance, a driving trip may be detected by the mobile device by periodically sampling acceleration data, speed data, and/or gyroscopic data and comparing this data to speed profiles, rotation profiles, and/or acceleration profiles consistent with driving behavior. GPS or LBS 224 may also be used to determine (or confirm) that the mobile device 220 is within a vehicle 210 during a driving trip, for instance, by comparing the time and location data of mobile device 220 to street map/navigational data. The current speed of the mobile device 220, which may be determined by tracking acceleration data over time and/or using GPS or LBS data, may be compared to speed limit data along the streets and roads driven to verify that the mobile device 220 is likely within a vehicle rather than be carried by a walker, runner, or bicyclists, etc.

Vehicle accidents may be detected by the mobile device 220, for example, by identifying a short spike in positive or negative acceleration readings from an accelerometer 223. In some cases, any acceleration reading over a predetermined threshold may be identified by an accident detection software application 222 as a potential accident. In other cases, a short spike in positive or negative acceleration may be identified as a potential accident only if the mobile device 220 has previously been determined to be in a vehicle being driven and/or only if the current location of the mobile device 220 corresponds to a street, highway, parking lots, or other location accessible to a vehicle 210. In certain examples, additional data such as audio or video data collected by the mobile device 220 and/or impact sensors or the mobile device 220 may be used to determine that the mobile device 220 is within a vehicle 210 that has been involved in an accident.

In some embodiments, rather than the mobile device 220 directly detecting a vehicle accident, the mobile device 220 may receive an indication of an accident from the vehicle 210. For instance, when approaching or entering a vehicle 210, the mobile device may be configured to establish communication with one or more vehicle based systems (e.g., 211-215), allowing the mobile device 220 to receive vehicle sensor data, diagnostic data, location data, V2V data, and any other data from the vehicle 210. In some cases, the personal mobile devices 220 of a vehicle's owner, family members or other frequent users of a vehicle 210 may be pre-authorized to connect and receive data from a vehicle 210 whenever the pre-authorized mobile devices 220 approach or enter the vehicle 210. In such examples, when a mobile device 220 is not pre-authorized to connect and receive data from a vehicle 210, a manual authorization process may be initiated at the mobile device 220 and/or at the vehicle 210 when the mobile device 220 approaches the vehicle 210, or the vehicle and/or mobile device 220 may be configured so that allow only a subset of the driving data/vehicle data may be provided from the vehicle 210 to the unauthorized (or guest) mobile device 220.

When a mobile device 220 is able to establish a connection and communication session with a vehicle 210, the mobile device 220 may receive data from one or more of the vehicle-based systems (e.g., 211-215), including driving data and accident data. In such cases, an accident detection application 222 executing on the mobile device 220 may receive sensor data from vehicle operation sensors 211 or other vehicle-based systems, such as a vehicle speed and acceleration data, a vehicle body impact indicator, an airbag deployment indicator, or any other vehicle data. The accident detection application 222 may analyze the accident indicators and/or other data received from the vehicle 210 to determine in step 301 that the vehicle has been involved in an accident.

Figure 4A:
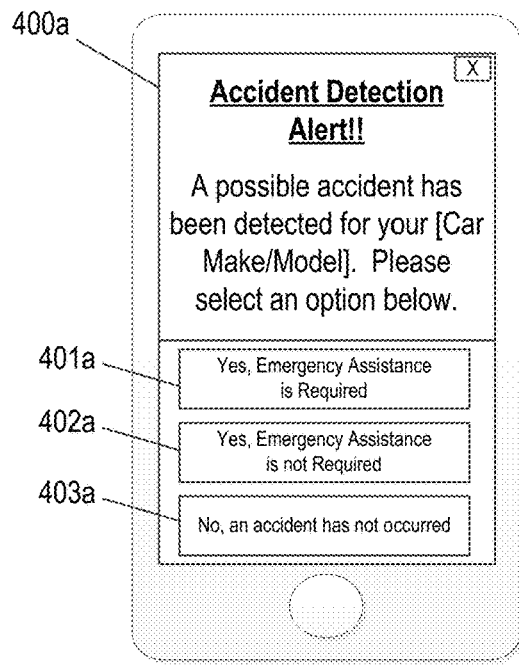
FIGS. 4A-4H are example user interface display screens of a mobile computing device illustrating various functionality and features of an accident detection and recovery system, according to one or more aspects of the disclosure.
Figure 4B:
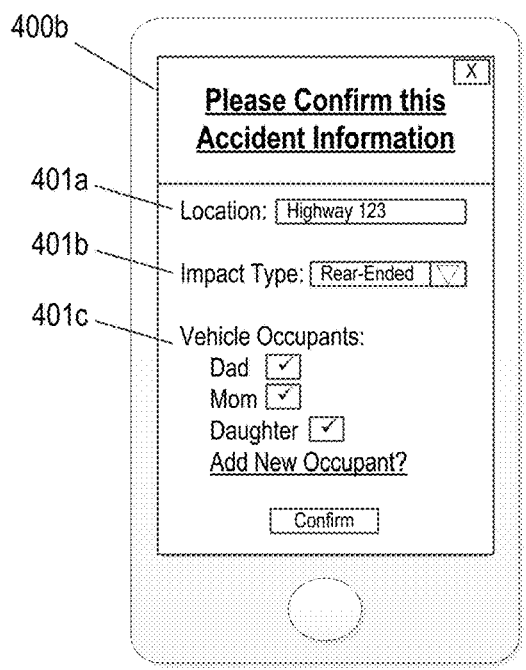

Referring to FIG. 4A, a mobile device 220 is shown displaying an example user interface screen generated by an accident detection and/or recovery application 222. In this example, application 222 has determined that the mobile device 220 is in a vehicle 210 that was potentially involved in an accident. As discussed above in step 301, this determination may be performed solely by the mobile device 220 or in conjunction with the vehicle 210 and/or other external devices (e.g., V2V systems in other vehicles 210, roadside cameras and traffic servers 250, etc.). In FIG. 4A, an accident detection alert 400a is displayed to the user of the mobile device 220. The accident detection alert 400a may be accompanied sound, vibration, and/or other notification technique to alert the user of the event. In this example, the make and model of the vehicle have also been identified and displayed in the alert (e.g., based on data received from the vehicle 210, insurance server 250a, etc.). In other examples, if the vehicle 210 involved in the accident cannot be determined automatically by the accident detection and/or recovery application 222, the application 222 may prompt the user to input the vehicle information (e.g., make, model, trim, year, features, etc.) into the mobile device.

In FIG. 4A, three response options are provided for the user of the mobile device 220 with the accident detection alert. The user may confirm that an accident has occurred and indicate that emergency assistance is required (401a), confirm that an accident has occurred and indicate that emergency assistance is not required (402a), or indicate that an accident has not occurred (403a). Such false positive determinations in step 301 may result from, for example, a user throwing or dropping their mobile device 220, or a vehicle accident in a first vehicle 210 that communicates in error with mobile devices 220 in different nearby vehicles.

In step 302, one or more accident characteristics may be received and/or determined corresponding to the accident identified in step 301. The accident characteristics in step 302 may be determined by and/or received from a mobile device 220, one or more vehicle-based systems 211-215 of a vehicle 210 involved in the accident, one or more vehicle-based systems 211-215 of other vehicles 210 near the accident, one or more external servers 250 (e.g., weather servers, traffic servers, road condition servers, etc.), or any combination of these devices. As discussed below, the accident characteristics received and/or determined in step 302 may be used to identify estimated/potential damages resulting from the accident. Thus, the accident characteristics received and/or determined in step 302 may include the number and types of each vehicle 210 involved in the accident (e.g., make, model, vehicle class, height, weight, etc.), descriptions of any other non-vehicle objects involved in the accident (e.g., posts, signs, trees, animals, bicyclists, pedestrians, etc.), the speed(s) of the vehicle(s) just before the accident, the location and angle of impact to/from each vehicle 210, the time and day of the accident, the accident location and type of road (e.g., highway, residential street, parking lot, etc.), and the traffic conditions, weather conditions, road conditions, visibility conditions, at the like, at the time of the accident. Additional accident characteristics received and/or determined in step 302 may include the numbers and identities of the driver and passengers in the vehicle 210, the seating locations of each passenger in the vehicle 210 at the time of the accident, and the presence and location of any bicycles, skies, snowboards, golf clubs, and other items of value in or on the vehicle at the time of the accident.

As noted above, the accident characteristics may be determined in step 302 by mobile devices 220, vehicles 210, and/or one or more external servers 250. For example, a mobile device 220 may use movement sensors 223 and GPS and LBS location systems 224 to determine vehicle speed at the time of the accident, angle of impact, accident time and location, etc. For accident characteristics such as the point of impact on the vehicle body, the force of the impact, and vehicle diagnostic data relating to the accident (e.g., airbags deployed, windows broken, fluids leaking, etc.), the mobile device 220 may receive these accident characteristics directly or indirectly from the vehicle 210 and/or vehicle-based devices (e.g., 211-215). For additional accident characteristics, such as the weather conditions, traffic conditions, road conditions and visibility conditions at the time and location of the accident, the mobile device may receive these accident characteristics directly or indirectly from one or more external servers 250.

In some examples, an accident detection and recovery application 222 may generate a list of the potential vehicle damages and repairs/inspections needed based on the accident characteristics received and/or determined in step 302. For instance, referring to FIG. 4B, an example user interface screen 400b is shown displaying a set of accident characteristics received or determined by the accident detection and recovery application 222 in step 302. In this example, the accident characteristics determined by the application 222 include the location of the accident 401b, the type of impact 402b, and the number/names of passengers in the vehicle 403b. In some implementations, a user interface screen 400b may be configured to allow the user to confirm the accident information that has been received or determined by the mobile device 220, and to allow the user to input addition accident information (e.g., passenger names and seating locations, descriptions of body damage or leaking fluids, information identifying the other vehicle(s) and driver(s) involved in the accident, etc.). In such cases, the accident characteristics determined in step 302, including accident data automatically determined by the mobile device 220, accident data received from various other devices, and any accident data input, edited, or confirmed by the user, may be stored in an accident report on the mobile 220 and/or transmitted to one or more other devices in the system 200 (e.g., an insurance server 250a).

In step 303, data relating to one or more vehicle and/or individuals in the accident may be retrieved by the accident detection and recovery application 222 of the mobile device 220. As discussed below in more detail, the vehicle data and/or individual data retrieved in step 303 may be used to identify and estimate potential medical damages and vehicle damages that may have occurred from the accident, and to determine accident recovery recommendations based on the damages. However, certain types of potential medical damages and vehicle damages, and the corresponding accident recovery recommendations, may be determined based only on the one or more accident characteristics retrieved in step 302 (e.g., vehicle types, vehicle speeds, impact types, accident location, passengers in car, etc.). Thus, step 303 may be optional in some cases.

The individual data retrieved in step 303 may include physical characteristics, medical data, and any other data relevant to determining potential damages or injuries to the driver or passengers in the vehicle 210 at the time of the accident. As discussed above in step 302, the number and identities of the vehicle's occupants during the accident may be determined automatically by mobile devices 220 (e.g., by assuming device owner is in vehicle, determining family and friends in vehicle based on communication with other mobile devices 220, driving routes, etc.) and/or by vehicle-based devices 210 (e.g., using vehicle operation settings, driving behaviors and profiles, driving routes, seat weight sensors, internal cameras and facial recognition software, etc.). Additionally, number and identities of the vehicle's occupants during the accident may be determined based on user input into a user interface screen on the mobile device 220 (e.g., a dropdown list of family members and friends, text boxes for inputting new passenger information, etc.).

Using the identifying information of the driver and passengers (e.g., names, addresses, dates of birth, relationship data, social security numbers, etc.), the accident detection and recovery application 222 may send a request to one or more external servers 250 to retrieve more detailed information about the individuals. For example, application 222 may contact an insurance server 250a, governmental server 250b, medical provider server 250b, social networking server 250b, or any other available data source 250b to retrieve the ages, physical attributes (e.g., height and weight), and medical histories and medical conditions (e.g., previous injuries, previous accidents, allergies, current medications, recent surgeries, pacemakers, etc.). Additionally, application 222 may contact an insurance server 250a or other data source to retrieve insurance coverages and policy details (e.g., automobile insurance types, liability limits, comprehensive limits, damage deductibles, number of previous accidents, etc.) for each of the vehicle occupants at the time of the accident.

In addition to individual data, vehicle data may be retrieved in step 303 corresponding to the vehicle(s) 210 involved in the accident. Vehicle information retrieved in step 303 may include for example, the type and physical characteristics of the vehicle (e.g., make, model, trim, year, engine specifications, optional features, paint color, etc.), current vehicle mileage, vehicle warranty information, vehicle maintenance records, previous vehicle accident records and insurance claims, etc. In order to retrieve such vehicle information in step 303, an accident detection and recovery application 222 on the mobile device 220 may send a request to an insurance server 250a, governmental vehicle database 250c, dealership vehicle database 250c, vehicle repair shop database 250c, or other data source, using one or more vehicle identifiers (e.g., VINs, license plate numbers, owner and registration address, insurance account numbers, etc.) to retrieve the detailed vehicle information. Additional vehicle information retrieved in step 303 may include data that is not specific to an individual vehicle, such as vehicle safety records, reliability data, depreciation and trade-in values for different vehicle makes, models, and years.

Steps 304-306, discussed below, relate to the determination of potential damages from the vehicle accident (step 304), the determination of accident recovery options and recommendations (step 305), and the generation and presentation of the potential damages and recovery options to the user (step 306). Several examples of user interface screens generated based on potential accident damages and accident recovery options are also shown in FIGS. 4C-4H, which are also discussed below in connection with steps 304-306.

In step 304, the accident characteristics determined in step 302 and/or the individual and vehicle data retrieved in step 303 may be analyzed to identify the types and amounts of potential damages resulting from the accident. The potential damages determined in step 304 may include medical damages (e.g., injuries and potential injuries) to occupants of the vehicle 210 or other individuals involved in the accident (e.g., occupants in other vehicles 210a-210c, bicyclists, pedestrians, etc.). Such medical damages may be based on the characteristics of the accident (e.g., the speed and direction of travel of the vehicle(s) just before the accident, the impact point on the vehicle 210, the model type, curb weight, and safety features and ratings of the vehicle(s) involved in the accident, which airbags were deployed by the vehicle 210, etc.), as well as information about the occupants of the vehicle 210 (e.g., seating positions within the vehicle 210, ages, heights and weights, medical histories and current medical conditions, etc.). For instance, an accident detection and recovery application 222 may compare the accident characteristics to different accident impact types and predetermined speed thresholds (e.g., rear impact>10 MPH, side impact>15 MPH, front impact>10 MPH, glancing impact>25 MPH, etc.) to determine if the vehicle occupants should be examined for potential back and neck damage and/or concussions. In some cases, the accident detection and recovery application 222 may determine and implement different speed impact thresholds (and other conditions for determining potential injuries) based on the specific individual data retrieved in step 303, for example, passengers of different ages (e.g., young children and elderly occupants may have lower impact thresholds), different seating positions or seat belt type/usage (e.g., backseat passengers, reclined passengers, passengers having only lap belts, and occupants not wearing seatbelts may have lower impact thresholds), different physical sizes (e.g., extremely tall, short, heavy, or light occupants may have higher or lower impact thresholds), and for occupants that have sustained previous injuries or other medical conditions (e.g., a passenger that recently sustained a broken arm, a passenger that was treated for extensive neck and back injuries from a previous car accident, etc.).

In addition to medical damages, the potential damages determined in step 304 may include property damages, in the form of damage to the vehicle 210, other vehicles 210a-210c involved in the accident, or other property that may potentially have been damaged in the accident (e.g., bicycles, street signs, posts, trees, fences, mailboxes, etc.). The potential damages to the vehicle 210 resulting from the accident may be based on the characteristics of the accident (e.g., the speed and direction of travel of the vehicle(s) just before the accident, the impact point on the vehicle 210, the model type, curb weight, and safety features of the vehicle(s) involved in the accident, which airbags were deployed by the vehicle 210, etc.), as well as information the general and specific vehicle data retrieved in step 303 (e.g., vehicle make, model, year, trim, mileage, previous accidents and repairs of the vehicle, the maintenance records of the vehicle, vehicle safety and reliabilities ratings, etc.). For instance, an accident detection and recovery application 222 may compare the accident characteristics to different accident impact types and predetermined speed thresholds (e.g., rear impact>15 MPH, side impact>5 MPH, front impact>10 MPH, glancing impact>5 MPH, etc.) to determine if the vehicle 210 is likely to have sustained damage. Multiple thresholds may be defined and implemented within the application 222 for different vehicle types (e.g., by make, model, and year), and for different severity levels of vehicle damages, such as a first speed impact threshold to determine if vehicle 210 is likely to have body damage, and a second higher speed impact threshold to determine if vehicle 210 is likely to have more serious structural damage. In some cases, the accident detection and recovery application 222 may determine and implement different speed impact thresholds (and other conditions for determining potential damages) based on vehicle-specific data such as previous accident records and maintenance history. For instance, a first vehicle 210a may be given a higher speed impact threshold for determining potential vehicle damage based on its regular maintenance history and the purchase of additional vehicle safety features, while a second vehicle 210b may be given a lower speed impact threshold based on one or more previous accident involving the vehicle during which the vehicle 210b may have incurred minor frame damage.

In step 305, a set of accident recovery options and/or recommendations may be determined based on the potential damages identified in step 304. As discussed above, the determination of accident recovery options and recommendations in step 305 may be performed by an accident detection and recovery application 222 executing on the mobile device 220. In other examples, this step (and some or all of the other functionality discussed in FIG. 3) may be performed by mobile devices 220, vehicle-based systems (e.g., 211-215), one or more external servers (e.g., an insurance server 250a), and/or any combination of the hardware and software components of these devices.

The accident recovery options and recommendations determined in step 305 may be based on the potential damages identified in step 304. For example, the recovery options determined in step 305 for potential medical damages may include general recommended medical care, and specific recommendations of appropriate medical care providers and facilities based on the types of injuries potentially sustained and the injured individuals. The recovery options for vehicle damage and other property damage also may be based on the potential damages identified in step 304. For example, the recovery options determined in step 305 for potential vehicle damages may correspond to optional and recommended repairs of the potential vehicle damages.

The accident recovery options and recommendations determined in step 305 also may be based on the time, day, and geographic location of the accident. For example, certain medical care providers and facilities, vehicle repair shops, alternative transportation options, and various other services may or may not be current available to the vehicle's occupants depending on their location and the current time. Accordingly, both general and specific accident recovery recommendations may take into account the time and location of the accident, as well as other factors such as weather and visibility conditions, road type (e.g., street or highway), the crime rate in the neighborhood of the accident, etc.

Additionally, the accident recovery options and recommendations determined in step 305 also may be based on the insurance coverage, policy details, and other insurance factors associated with the vehicle 210, other vehicles 210a-210c involved in the accident, and any the insurance coverages associated with the individual vehicle occupants (e.g., health insurance, home and property insurance, personal or professional liability insurance, etc.) As discussed below in more detail, a user's accident recovery options and recommendations for both potential injuries and potential property damage may depend on the insurance policies and coverages of the individuals and vehicles involved in the accident.

In step 306, one or more user interface screens providing accident detection and/or recovery information are generated and displayed to the user. The user interface screens may be generated and displayed by the mobile device 220, the vehicle 210 (e.g., via a dashboard display, navigation system display, etc.), or a combination of devices in the accident detection and recovery system 200. The accident detection and/or recovery information provided to the user in step 306 may include any combination of the accident characteristics determined in step 302, the vehicle and/or individual data determined in step 303, the potential accident damages determined in step 304, and the accident recovery options and recommendations determined in step 305. Several examples of user interface screens providing accident detection and/or recovery information are shown in FIGS. 4C-4H, discussed below.

Figure 4C:
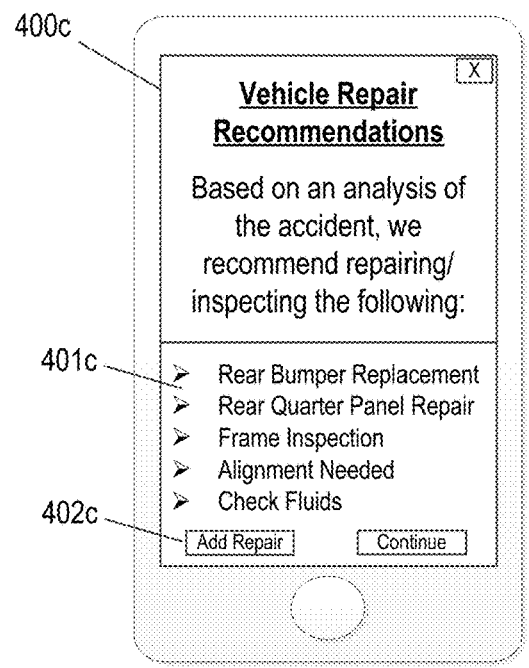

Referring now to FIG. 4C, an example user interface is shown displaying a vehicle repair recommendation screen 400c. In this example, after detecting a vehicle accident, and retrieving and analyzing various data related to the accident, a list of recommended vehicle repairs 401c has been determined and displayed on the mobile device 220. In some cases, the mobile device 220 may receive the list of vehicle repairs 401c from an internal diagnostic system of the vehicle 210. As discussed above, the vehicle sensors 211 and other vehicle-based systems may collect the vehicle damage information after an accident and transmit the data to the user's mobile device 220. In other examples, an accident detection and recovery application 222 of the mobile device 220 may list of recommended vehicle repairs 401c without receiving the vehicle damages from the vehicle 210. For instance, the application 222 may use the accident characteristics (e.g., vehicle speed and orientation, impact location, etc.), and the vehicle type to determine the list 401c of potential vehicle damages from the accident. In other cases, the application 222 may retrieve additional vehicle information, such as previous accident records and vehicle repair/maintenance data to determine the list 401c of potential vehicle damages.

As shown in FIG. 4C, the list of potential vehicle damages and/or recommended vehicle repairs from the accident may be manually edited by the user of the mobile device 220. For example, the accident detection and recovery application 222 may automatically generate and display an initial list of potential vehicle damages and/or recommended vehicle repairs 401c. The application 222 then may allow the user to add additional vehicle damages that were not identified by the automatic processes (e.g., using button 402c), and to remove any potential vehicle damages from the list 401c that were not actually damaged or that the user does not wish to repair (e.g., by selecting and deleting the items from the list 401c).

Figure 4D:
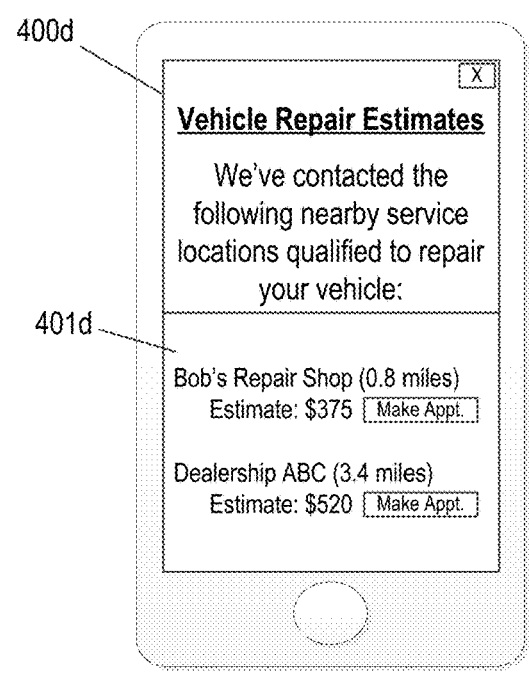

Referring now to FIG. 4D, another example user interface is shown displaying a list of vehicle repair estimates 400d. In this example, after determining a list of recommended or desired vehicle repairs 401c, which may be determined automatically and/or manually as discussed above, the accident detection and recovery application 222 may identify one or more qualified repair locations and obtain estimates for repairing the damage to the vehicle 210. The accident detection and recovery application 222 may determine the qualified repair locations based on, for example, the vehicle type (e.g., make, model, year, etc.) and the vehicle damage (e.g., body damage, engine repairs, tire replacements, etc.). Additionally, in some cases, the application 222 may identify nearby repair shops using the vehicle's current location, or may identify only those repair shops that accept the insurance coverage associated with the vehicle 210 and/or individual user. In order to determine the vehicle estimate amounts from the different repair shops, dealerships, etc., the accident detection and recovery application 222 may contact the repair location server 250d or other online services configured to provide vehicle repair estimates in real time or near real time.

Figure 4E:
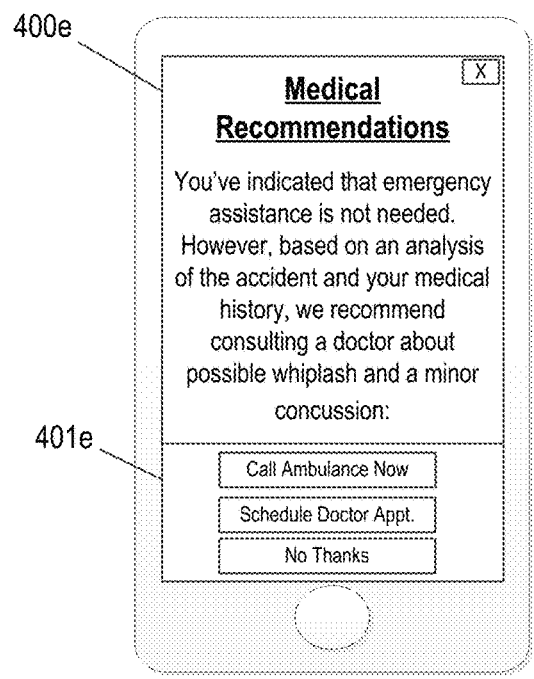

Referring now to FIG. 4E, another example user interface is shown displaying a medical recommendations screen 400e. In this example, the accident detection and recovery application 222 has determined that the user of the mobile device 220 may be at risk for suffering from back or neck injuries, or having a concussion, from the vehicle accident. In this example, the application 222 may determine that the user is at risk of having whiplash or a concussion based on the accident characteristics (e.g., vehicle speed, type and angle of impact, etc.), the type of vehicle(s) 210 involved in the accident, and the medical history of the user (e.g., previous vehicle accidents, previous concussions, etc.). In addition to the displayed medical recommendations 400e, the user interface in FIG. 4E also displays three interactive user response buttons 401e that may allow the user to contact an ambulance for immediate medical attention, schedule a doctor's appointment for non-urgent medical care, or decline the medical recommendations generated by the application 222.

Figure 4F:
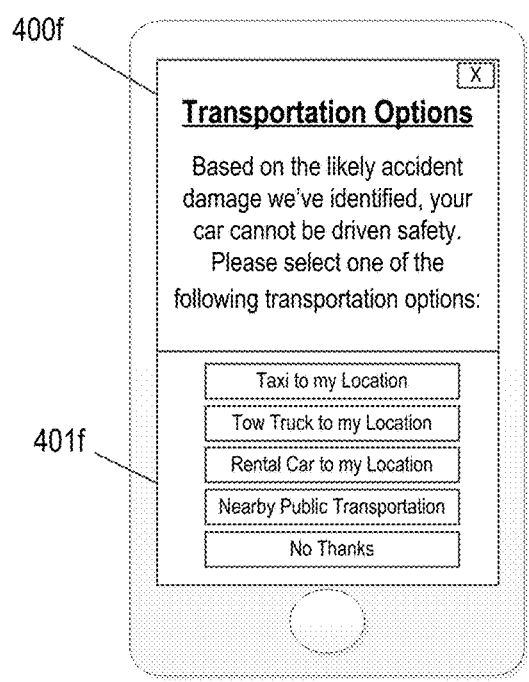

Referring now to FIG. 4F, another example user interface is shown displaying a transportation options screen 400f. In this example, the accident detection and recovery application 222 has determined that the vehicle 210 has sustained damage from the accident making the vehicle potentially undrivable. Accordingly, the application 222 in this example may use the current location of the mobile device 220 (i.e., the accident location), the current time, current weather conditions, and the existence of various nearby businesses or facilities to identify and recommend one or more transportation options for the user of the mobile device 220. In this example, the accident detection and recovery application 222 has identified and displayed a list 401f of possible transportation options available to the user, in the event that the vehicle 210 is undrivable, including a taxi, tow truck, rental car, or public transportation. The user may select any of these options via the user interface screen 400f to obtain additional information and/or contact the transportation provider.

Figure 4G:
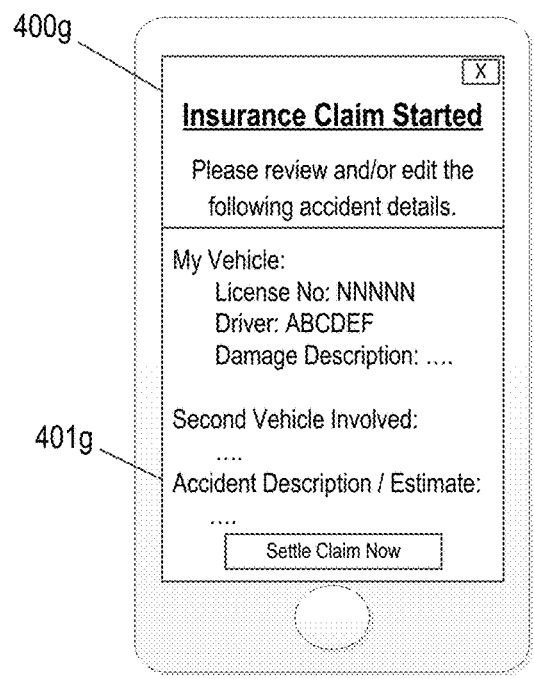

Referring now to FIG. 4G, another example user interface is shown displaying an insurance claim review and settlement screen 400g. In this example, the accident detection and recovery application 222, alone or in conjunction with an insurance provider server 250a, has automatically initiated an insurance claim based on the accident. To start an insurance claim, the application 222 may initiate an electronic claim process and populate one or more electronic claim forms (e.g., 401g) with the vehicle data for the vehicle(s) 210 involved in the accident, the accident description, accident damage types, injury or repair estimates, and the like. In certain examples, the vehicle data shown in FIG. 4G may be manually input by the user into the application 222 on the mobile device 220. In other examples, the vehicle data may be transmitted from the vehicles 210 involved in the accident, via one or more vehicle-based systems (e.g., V2V communication system 212, telematics device 213, etc.). Similarly, the accident description in the electronic claim form 401g may be manually input by the user, or may be automatically generated by the application 222 using the determined accident characteristics, the retrieved vehicle data and individual data, etc. In some examples, the accident detection and recovery application 222 may automatically initiate an insurance claim and populate the electronic claim forms based on the accident data determined in steps 302-305, and then may present the pre-populated insurance claim forms to the user for revision and/or confirmation. After reviewing and confirming the user may select an option to settle the claim (e.g., the "Settle Claim Now" button).

Although the example shown in FIG. 4G relates to initiating insurance claims, in other examples the accident detection and recovery application 222 may determine that a vehicle 210 is totaled, and may initiate a title transfer process rather than an insurance claim process. For instance, if the application 222 determines that the damages to the vehicle 210 (or the likely and/or potential damages) from the accident are greater than the value of the vehicle 210, then the application 222 may, alone or in conjunction with the insurance server 250a and/or other external devices 250) commence and electronic process to transfer the vehicle title to the insurance provider or a salvage facility.

Figure 4H:
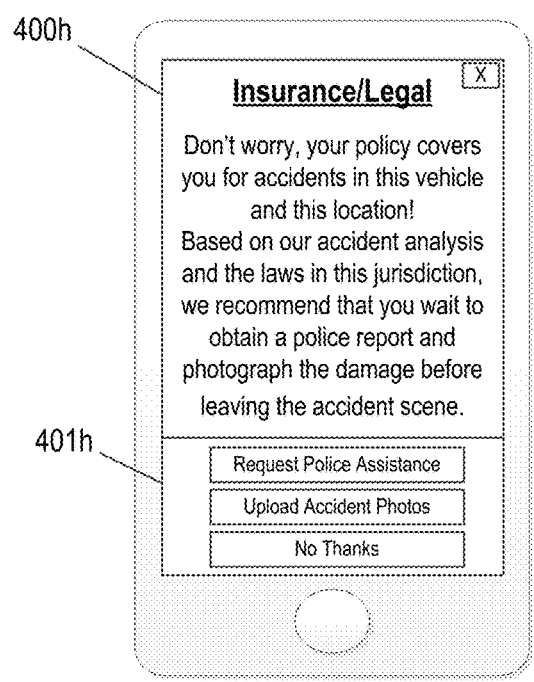

Referring now to FIG. 4H, another example user interface is shown displaying an insurance and legal services screen 400h. In this example, the accident detection and recovery application 222 has determined that the vehicle and/or user are covered by an insurance policy with respect to the accident. The determination an insurance policy will cover a vehicle accident in this example may be based on, for example, the vehicle 210 involved in the accident, the driver and/or passengers in the vehicle 210, the coverages, terms, and conditions of the insurance policies covering the vehicle and/or occupants, the accident characteristics and potential damages, and the location or jurisdiction of the accident. In this example, based on the vehicle 210 and the individuals involved in the accident, the accident characteristics, and the accident location, the accident detection and recovery application 222 has determined that the accident will be covered by an insurance policy, and also has determined one or more legal recommendations 401h, which may be selected by the user.

While the aspects described herein have been discussed with respect to specific examples including various modes of carrying out aspects of the disclosure, those skilled in the art will appreciate that there are numerous variations and permutations of the above described systems and techniques that fall within the spirit and scope of the invention.

What is claimed is:

1. A mobile computing device, comprising:
one or more processors;
one or more hardware memory units; and
one or more network interfaces, wherein the mobile computing device is configured to access and employ the one or more hardware memory units and processors to:
receive, via the one or more network interfaces and via a wireless communication network, an accident detection and recovery application; and
execute the accident detection and recovery application, executing the accident detection and recovery application including executing computer-readable instructions to:
receive current location and time data from a Global Positioning System (GPS) associated with the mobile computing device;
determine, using movement sensors within the mobile computing device, that the mobile computing device is within a first vehicle, the movement sensors measuring at least one of a speed of the first vehicle, a vibration force on the first vehicle while the first vehicle is in motion, and a direction of the first vehicle while the first vehicle is in motion;

determine, based on the current location data, that the current location data corresponds to an area accessible to a vehicle;

after determining that the mobile computing device is within the first vehicle and that the current location data corresponds to the area accessible to the vehicle, determine, based on a spike in positive or negative accelerometer readings, that the first vehicle was involved in an accident;

after determining that the vehicle was involved in an accident, determine, based on receiving communications from a second vehicle via a short-range communication protocol, that the second vehicle is in proximity to the first vehicle;

after determining that the second vehicle is in proximity to the first vehicle, receive, from the second vehicle, sensor data wherein the sensor data is obtained from one or more sensors within the second vehicle;

after receiving the sensor data from the second vehicle, determine, based on the received sensor data corresponding to the accident and data received from the at least one of the movement sensors and location sensors, one or more accident characteristics associated with the accident;

determine at least one of a type of potential damages or an amount of the potential damages associated with the accident, based on the one or more accident characteristics; and generate and display an accident recovery user interface on the mobile computing device, the accident recovery user interface including medical recommendations based on the at least one of the type or the amount of the potential damages, the medical recommendations including one or more interactive graphical elements to allow a user of the mobile computing device to accept or decline the medical recommendations.

2. The mobile computing device of claim 1, wherein determining the one or more accident characteristics associated with the accident comprises:

receiving, from a vehicle-based computing device of the first vehicle, at least one of:
  a speed of the first vehicle at a time of the accident;
  an area of impact on the first vehicle during the accident; and
  a number of passengers in the first vehicle at the time of the accident.

3. The mobile computing device of claim 1, wherein determining that the mobile computing device is in the first vehicle further includes:

retrieving and analyzing data from at least one of:
  an accelerometer of the mobile computing device;
  a speedometer of the mobile computing device; and
  the Global Positioning System (GPS) or other location-based service (LBS) of the mobile computing device.

4. The mobile computing device of claim 1, wherein determining the type of the potential damages or the amount of the potential damages associated with the accident further includes:

retrieving, from an external computer server, via the one or more network interfaces, at least one of physical attribute data or medical history data for one or more occupants of the first vehicle; and determining at least one of a type or amount of potential medical damages to the one or more occupants of the first vehicle based on the retrieved at least one of physical attribute data or medical history data of the one or more occupants of the first vehicle and based on the one or more accident characteristics.

5. The mobile computing device of claim 1, wherein generating and displaying the accident recovery user interface comprises:

determining one or more insurance coverage characteristics applicable to the accident; and determining a recovery recommendation based on the one or more insurance coverage characteristics applicable to the accident, and based on the one or more accident characteristics.

6. The mobile computing device of claim 5, wherein the mobile computing device is further configured to access and employ the one or more hardware memory units and the one or more processors to:

initiate at least one of:
  an insurance claim;
  a title transfer process; and
  a vehicle damage repair estimate,
  wherein the initiation of the insurance claim, the title transfer process, or the vehicle damage repair estimate is based on the determined type or the amount of the potential damages associated with the accident, and the one or more insurance coverage characteristics applicable to the accident.

7. The mobile computing device of claim 1, wherein the type of the potential damages is further based on seating positions of one or more occupants of the vehicle.

8. A method, comprising:

receiving, by a mobile computing device and via a wireless communication network, an accident detection and recovery application; and executing, by the mobile computing device, the accident detection and recovery application, executing the accident detection and recovery application including executing a series of computer-readable instructions to:

receive, from a Global Positioning System (GPS) associated with the mobile computing device, current time and location data of the mobile computing device;

determine, by the mobile computing device and using movement sensors within the mobile computing device, that the mobile computing device is in a first vehicle, the movement sensors measuring at least one of a speed of the first vehicle, a vibration force on the first vehicle while the first vehicle is in motion, and a direction of the first vehicle while the first vehicle is in motion;

determine, based on the current location data, that the current location data corresponds to an area accessible to a vehicle;

after determining that the mobile computing device is within the first vehicle and that the current location data corresponds to the area accessible to the vehicle, determine, based on a short spike in positive or negative accelerometer readings, that the first vehicle was involved in an accident;

after determining that the vehicle was involved in an accident, determine, based on receiving communications from a second vehicle via a short-range communication protocol, that the second vehicle is in proximity to the first vehicle;

after determining that the second vehicle is in proximity to the first vehicle, receive, by the mobile computing device from the second vehicle, sensor data wherein the sensor data is obtained from one or more sensors within the second vehicle;

after receiving the sensor data from the second vehicle, determine, by the mobile computing device and based on the received sensor data corresponding to the accident and on data received from the at least one of the movement sensors and location sensors, one or more accident characteristics associated with the accident: determine, by the mobile computing device, at least one of a type of potential damages or an amount of the potential damages associated with the accident, based on the one or more accident characteristics; and generate and display, by the mobile computing device, an accident recovery user interface, the accident recovery user interface including medical recommendations based on the at least one of the type or the amount of the potential damages, the medical recommendations including one or more interactive graphical elements to allow a user of the mobile computing device to accept or decline the medical recommendations.

9. A method, comprising:

receiving, by a mobile computing device and via a wireless communication network, an accident detection and recovery application; and executing, by the mobile computing device, the accident detection and recovery application, executing the accident detection and recovery application including executing a series of computer-readable instructions to:

receive, from a Global Positioning System (GPS) associated with the mobile computing device, current time and location data of the mobile computing device;

determine, by the mobile computing device and using movement sensors within the mobile computing device, that the mobile computing device is in a first vehicle, the movement sensors measuring at least one of a speed of the first vehicle, a vibration force on the first vehicle while the first vehicle is in motion, and a direction of the first vehicle while the first vehicle is in motion;

determine, based on a current location data, that the current location data corresponds to an area accessible to a vehicle;

after determining that the mobile computing device is within the first vehicle and that the current location data corresponds to the area accessible to the vehicle, determine, based on a short spike in positive or negative accelerometer readings, that the first vehicle was involved in an accident;

after determining that the vehicle was involved in an accident, determine, based on receiving communications from a second vehicle via a short-range communication protocol, that the second vehicle is in proximity to the first vehicle;

after determining that the second vehicle is in proximity to the first vehicle, receive, by the mobile computing device from the second vehicle, sensor data wherein the sensor data is obtained from one or more sensors within the second vehicle;

after receiving the sensor data from the second vehicle, determine, by the mobile computing device and based on the received sensor data corresponding to the accident and on data received from the at least one of the movement sensors and location sensors, one or more accident characteristics associated with the accident;

determine, by the mobile computing device, at least one of a type of potential damages or an amount of the potential damages associated with the accident, based on the one or more accident characteristics; and generate and display, by the mobile computing device, an accident recovery user interface, the accident recovery user interface including medical recommendations based on the at least one of the type or the amount of the potential damages, the medical recommendations including one or more interactive graphical elements to allow a user of the mobile computing device to accept or decline the medical recommendations.

10. The method of claim 9, wherein determining the one or more accident characteristics associated with the accident comprises:

receiving, from a vehicle-based computing device of the first vehicle, at least one of:
a speed of the first vehicle at a time of the accident;
an area of impact on the first vehicle during the accident; and
a number of passengers in the first vehicle at the time of the accident.

11. The method of claim 9, wherein determining that the mobile computing device is in the first vehicle further includes:

retrieving and analyzing data from at least one of:
an accelerometer of the mobile computing device;
a speedometer of the mobile computing device; and
the Global Positioning System (GPS) or other location-based service (LBS) of the mobile computing device.

12. The method of claim 9, wherein determining the type of the potential damages or the amount of the potential damages associated with the accident further includes:

retrieving, from an external computer server, at least one of physical attribute data or medical history data for one or more occupants of the first vehicle; and determining at least one of a type or amount of potential medical damages to the one or more occupants of the first vehicle, based on the retrieved at least one of physical attribute data or medical history data of the one or more occupants of the first vehicle and based on the one or more accident characteristics.

13. The method of claim 9, wherein generating and displaying the accident recovery user interface comprises:

determining one or more insurance coverage characteristics applicable to the accident; and determining a recovery recommendation based on the one or more insurance coverage characteristics applicable to the accident, and based on the one or more accident characteristics.

14. The method of claim 13, further comprising:

initiating, by the mobile computing device, at least one of:
an insurance claim;
a title transfer process; and
a vehicle damage repair estimate,
wherein the initiation of the insurance claim, the title transfer process, or the vehicle damage repair estimate is based on the at least one of the type or the amount of the potential damages associated with the accident, and the one or more insurance coverage characteristics applicable to the accident.

15. The method of claim 9, wherein the type of the potential damages is further based on seating positions within the vehicle.

16. A system, comprising:
a mobile computing device, comprising:
a processing unit;
a hardware memory unit; and
a wireless network interface;
a vehicle-based computing device of a first vehicle, comprising:
a second processing unit;
a second hardware memory unit; and
a network interface configured to receive sensor data from vehicle sensors of the first vehicle; and
one or more computer servers located at an external location from the mobile computing device and the first vehicle and communicatively coupled to the mobile computing device via a communication network, each said one or more computer server comprising:
one or more processors;
one or more nonvolatile hardware memory units; and
one or more networking components,
wherein the mobile computing device further includes an accident detection and recovery application executing in a background of the mobile computing device, the accident detection and recovery application configured to access and employ the hardware memory unit and processor of the mobile computing device to:
determine that the mobile computing device is within the first vehicle based on communication with the vehicle-based computing device of the first vehicle;
receive current location and time data from a Global Positioning System (GPS) associated with the mobile computing device;
determine, based on the current location of the first vehicle, that the current location corresponds to an area accessible to a vehicle;
determine, using movement sensors within the mobile computing device, that the mobile computing device is within the first vehicle, the movement sensors measuring at least one of a speed of the vehicle, a vibration force on the vehicle while the vehicle is in motion, and a direction of the vehicle while the vehicle is in motion;
after determining that the mobile computing device is within the first vehicle and that the current location corresponds to the area accessible to the vehicle, determine, based on a short spike in positive or negative accelerometer readings, that the first vehicle was involved in an accident;
after determining that the vehicle was involved in an accident, determine, based on receiving communications from a second vehicle via a short-range communication protocol, that the second vehicle is in proximity to the first vehicle;
after determining that the second vehicle is in proximity to the first vehicle, receive, from the second vehicle, sensor data wherein the sensor data is obtained from one or more sensors within the second vehicle;
after receiving the sensor data from the second vehicle, determine, based on the received sensor data and data received from the movement sensors and location sensors one or more accident characteristics associated with the accident;
determine at least one of a type of potential damages or an amount of potential damages associated with the accident based on the one or more accident characteristics;
retrieve, from the one or more computer servers, accident recovery data based on at least one of:
data identifying the first vehicle;
data identifying a user of the mobile computing device; or
the one or more accident characteristics, and
display an accident recovery user interface on the mobile computing device, the accident recovery user interface including medical recommendations based on the accident recovery data retrieved from the one or more computer servers and recovery recommendations based on the at least one of the type or the amount of the potential damages, the medical recommendations including one or more interactive graphical elements to allow a user of the mobile computing device to accept or decline the medical recommendations.

17. The system of claim 16, wherein retrieving the accident recovery data from the one or more computer servers comprises:
transmitting, to the one or more computer servers, identifying information corresponding to one or more occupants of the first vehicle; and
receiving, from the one or more computer servers, at least one of physical attribute data or medical history data for the one or more occupants of the first vehicle.

18. The system of claim 16, wherein retrieving the accident recovery data from the one or more computer servers comprises:
transmitting the one or more accident characteristics to a vehicle repair server; and
receiving, from the vehicle repair server, a vehicle damage repair estimate.

19. The system of claim 16, wherein determining the one or more accident characteristics associated with the accident comprises:
receiving sensor data of the first vehicle, from the vehicle-based computing device of the first vehicle; and
analyzing the sensor data of the first vehicle to determine the one or more accident characteristics.

20. The system of claim 16, wherein the determined one or more accident characteristics comprise at least one of:
a speed of the first vehicle at a time of the accident;
an area of impact on the first vehicle during the accident; and
a number of passengers in the first vehicle at the time of the accident.

* * * * *